(12) United States Patent
Dekel et al.

(10) Patent No.: US 8,774,902 B2
(45) Date of Patent: Jul. 8, 2014

(54) METHOD OF INFRARED THERMOGRAPHY FOR EARLIER DIAGNOSIS OF GASTRIC COLORECTAL AND CERVICAL CANCER

(75) Inventors: Ben Zion Dekel, Hadera (IL); Nathan Blaunshtein, Beer Sheva (IL); Arkadii Zilberman, Beer Sheva (IL)

(73) Assignee: Passive Imaging Medical Systems Engineering Ltd. (PIMS), Tel Aviv (IL)

( * ) Notice: Subject to any disclaimer, the term of this patent is extended or adjusted under 35 U.S.C. 154(b) by 1329 days.

(21) Appl. No.: 11/695,028

(22) Filed: Apr. 1, 2007

(65) Prior Publication Data

US 2007/0282190 A1    Dec. 6, 2007

Related U.S. Application Data (60) Provisional application No. 60/809,834, filed on Jun. 1, 2006.

(51) Int. Cl.
*A61B 6/00* (2006.01)

(52) U.S. Cl.
USPC .......................... 600/474; 600/475; 600/476

(58) Field of Classification Search
USPC .................................. 600/407, 430, 473–478
See application file for complete search history.

(56) References Cited

U.S. PATENT DOCUMENTS

| | | | | |
|---|---|---|---|---|
| 4,557,272 A | * | 12/1985 | Carr | ............................... 600/549 |
| 5,539,207 A | * | 7/1996 | Wong | ....................... 250/339.08 |
| 5,876,995 A | | 3/1999 | Bryan | |
| 5,900,632 A | * | 5/1999 | Sterling et al. | ............ 250/339.03 |
| 6,091,984 A | * | 7/2000 | Perelman et al. | .............. 600/476 |
| 6,975,898 B2 | | 12/2005 | Seibel | |
| 7,172,553 B2 | | 2/2007 | Ueno et al. | |
| 2001/0055462 A1 | * | 12/2001 | Seibel | ........................... 385/147 |
| 2004/0236225 A1 | * | 11/2004 | Murphy et al. | ................ 600/473 |

OTHER PUBLICATIONS

H.P. Wang H.C. Wang Y.J. Huang *Microscopic FTIR Studies of Lung Cancer Cells in Pleural Fluid* The Science of the Total Environment 204 (1997) 283-287 Jun. 1997.

Christodoulos Stefanadis, Christina Chrysohoou, Demosthenes B. Panagiotakos, Elisabeth Passalidou, Vasiliki Katsi, Vlassios Polychronopoulos, and Pavlos K. Toutouzas. *Temperature differences are associated with malignancy on lung lesions: a clinical study* Bio Med Central pp. 1-5 Jan. 6, 2003.

Ying Yang, Josep Sule'-Suso, Ganesh D. Sockalingurn, Gregory Kegelaer, Michel Manfait, Alicia J el Haj, *Study of Tumor Cell Invasion by Fourier Transform Infrared Microspectroscopy* Biopolymers vol. 78 pp. 311-317 (2005).

(Continued)

*Primary Examiner* — Unsu Jung
*Assistant Examiner* — Joseph M Santos Rodriguez
(74) *Attorney, Agent, or Firm* — Mark M. Friedman (57) ABSTRACT

A device and method to diagnose an internal abnormality in a living subject by sensing a passively occurring electromagnetic radiation signal associated with the abnormality and inside an orifice of the subject. Diagnosis includes detection, imaging or identification of the abnormality. An instrument is used either to bring a sensor into the orifice or to transmit the signal to a sensor located outside of the orifice. An example of the instrument includes a prior art endoscope.

8 Claims, 8 Drawing Sheets

(56) References Cited

OTHER PUBLICATIONS

Angelique Brooks, Natalia L. Anasyeva, Vladimir Makhine, Reinhard F. Bruch, Sergei F. Kolyakov, Slava Artjushenko and Leonid N. Butvina *New Method for Investigations of Normal Human Skin Surfaces in vivo Using Fiber Optic Evanescent Wave Fourier Transform Infrared Spectrosccopy(Few FTIR)* Dec. 23, 1998 pp. 221-229.

Naoko Fujioka, MD,PhD, Yuji Morimoto,MD PhD, Tsunenori Arai, PhD, Makoto Kikuchi PhD *Discrimination between normal and malignant human gastric tissues by fourier transform infrared spectroscopy*. Nov. 13, 2003 Cancer Detection and Prevention 28 (2004) pp. 32-36.

M. Gniadecka, H.C. Wulf N. Nymark Mortensen, *Diagnosis of Basal Cell Carcinoma by Raman Spectroscopy 1997* Journal of Raman Spectroscopy vol. 28. 125-129.

Christodoulos Stefanadis, Emmanouel Parskevas, Demosthenes B. Panaiotakos, Demetrios Xynopoulos, Dimitris Dimitroulopoulos, Kalliopi Petraki, Constantina Papadimitriou, Kyriakos Karoutos, Christos Pitsavos, Pavlos K. Toutowas *Thermal Hetreogeneity Constitutes a marker for the detection of malignant gastric lesions* In Vivo J Clin Gastroenterol 2003 pp. 215-218.

Brigitte Mayinger et al. Evaluation of in vivo endoscopic autofluorescence spectroscopy in gastric cancer vol. 59 No. 2 2004 191-198.

* cited by examiner

From Naoko Fujioka, Yuji Morimoto, Tsunenori Arai, Makoto Kikuchi, "Discrimination between normal and malignant human gastric tissues by Fourier transform infrared spectroscopy", Cancer Detection and Prevention 28, 32–36, (2004)

METHOD OF INFRARED THERMOGRAPHY FOR EARLIER DIAGNOSIS OF GASTRIC COLORECTAL AND CERVICAL CANCER

This is a continuation-in-part of U.S. Provisional Patent Application No. 60/809,834, filed Jun. 1, 2006.

FIELD AND BACKGROUND OF THE INVENTION

The present invention relates to a method and device to detect and identify pathologies inside orifices of a living subject and more specifically to a method and device to detect and identify cancer. Particular embodiments are configured for detection of colon cancer, cervical cancer, lung cancer, cancer of the esophagus, and stomach cancer. More specifically the present invention relates to a method and device including passive detection and identification of different kinds of internal tumors, lesions and cancers by combined analyses of visible and infrared optical signals based on integral and spectral regimes for detection and imaging leading to early warning and treatment of potentially dangerous conditions.

A few common cancers associated with orifices and the current art methods of diagnosis follow:

Gastric cancer is the seventh most frequent cause of cancer mortality in the US. The main screening methods for gastric cancer are:

Upper endoscopy imaging—A small visible spectrum camera and light source are attached to a flexible guide and inserted through the throat and into the stomach of a patient. A doctor examines the resulting images to detect abnormalities. Some improvements such as zoom capable cameras are in development. Nevertheless, all current visible imaging techniques have a few significant limitations. Firstly, detection of abnormalities is subjective and dependent on the expertise and the alertness of the examining doctor. Furthermore, while observed images are useful for detecting abnormal lesions, positive identification requires a biopsy to determine the lesions' status.

Endoscopic confocal microscopy—A conventional visible light endoscope is fitted with a probe capable of producing microscopic images. A pathologist uses the microscopic images to identify cancer in-vivo (without requiring examination of tissue in a biopsy). The technique is still in the stage of development and is currently exceedingly expensive. Furthermore, the method is based solely on visible inspection by a doctor and therefore the detection and identification are subjective and dependent on the alertness and subjective judgment of the examining doctor. Also, since the field of few the microscopic image is about 300 µm, there is a danger (depending on the expertise of the operator) that the microscopic imaging will miss an important feature of the abnormality.

Barium upper gastrointestinal radiography—A patient drinks a barium-containing solution that coats the lining of the esophagus, stomach and first portion of the small intestine. Then the resulting distribution of the barium is measured using x-rays. In and of itself, this test is not accurate, but it is useful in helping to identify lesions detected using other tests.

Endoscopic ultrasound—A transducer probe placed into the stomach through the mouth or nose uses sound waves to produce images of internal organs. The transducer emits sound waves and detects the echoes bounced off internal organs. Endoscopic ultrasound is useful for staging depth of tumor invasion. Nevertheless, endoscopic ultrasound cannot be used to for early detection or identification of tumors because ultrasound cannot detect young tumors smaller than the wavelength of sound (of order 1 cm) and because many different objects produce similar ultrasound echoes.

Computed tomography (CT)—The subject is scanned with x-rays over successive cross-sections. The procedure produces good sensitivity and accuracy, but has the major drawback of exposing the subject to significant quantities of potentially dangerous x-radiation.

Positron emission tomography (PET)—Radioactive glucose is injected into the subject's vein. Because cancers use sugar much faster than normal tissues, locations of high concentrations of the radioactive glucose are associated with cancer. Thus, by scanning the subject one can spot cancer that has spread beyond the stomach. PET is a useful test for staging the cancer. Nevertheless, PET scans are currently unable to detect or identify stomach cancer in its early stages.

Magnetic resonance imaging (MRI)—The subject is scanned using radio waves after exposure to strong magnets. A computer translates the pattern of radio waves given off by the tissues into a very detailed image of parts of the body. The procedure is extremely expensive and at present MRI appears to perform well in evaluating the local and distant extents of cancer but less well at detecting unsuspected primary tumors.

Endoscopic auto fluorescence spectroscopy—A new technique based on active excitation of tissue by applying UV light via an endoscope. Endogenous visible fluorescence spectra emitted by the tissue is collected with a fiber optic probe and analyzed with a spectrograph. While auto fluorescence spectroscopy has shown promise when applied to detection of skin cancer, auto fluorescence spectroscopy has disadvantages in internal studies. Firstly auto fluorescence spectroscopy requires subjecting potentially sensitive internal tissues to ultraviolet light stimulation. Secondly, auto fluorescence signals are masked by reflected visible light. Thus current art reflected light measurements cannot be made simultaneously to auto fluorescence measurements. This means that auto fluorescence cannot be used in addition to current reflected light techniques for improved detection of abnormalities. Attempts to apply auto fluorescence for diagnosis of internal abnormalities [see Mayinger, B., M. Jordan, T. Horbach, et al., "Evaluation of in vivo endoscopic auto fluorescence spectroscopy in gastric cancer", Gastrointestinal Endoscopy, vol. 59, No. 2, 2004, pp. 191-198] have not provided satisfactory results.

Colorectal cancer is the third most common malignant neoplasm worldwide; the following methods are used for colorectal screening:

Fecal Occult Blood test—The presence of hidden blood is detected in the stool. Blood in the stool that is not visible is often the first warning sign that a person has a colorectal disorder. The disadvantages of this method are that it detects blood in stool, but not its cause and False-positive and false negative results are common. Thus a more sensitive and precise test is needed.

Flexible sigmoidoscopy and colonoscopy—These techniques are similar to upper endoscopy except that the endoscope is called a sigmoidoscope or colonoscope and is inserted in the rectum rather than the throat. These techniques can discover 50% to 65% of polyps and are subject to all of the limitations of upper endoscopy.

Virtual Colonoscopy (CT Colonoscopy)—Refers to examination of computer-generated images of the colon from data obtained by CT or MRI machines. The performance of this non-invasive method depends heavily on the size of the lesion; it can miss polyps smaller than 10 mm and generally suffers from the limitations of CT and MRI imaging mentioned above.

DNA Mutation in the Stool—This new non-invasive method is based on the detection of mutations in faucal DNA. At present the cost of this technique is high and sensitivity results are the same as colonoscopy.

Barium Enema—Flow of barium is monitored on an x-ray fluorescence screen. This method has a low rate of detection even of large adenomas, but the technique is valuable in cases in which the colonoscopy does not reach the lesion.

Cervical cancer is cancer of the uterine cervix, the portion of the uterus attached to the top of the vagina. Ninety percent of cervical cancers arise from the flattened or "squamous" cells covering the cervix. Most of the remaining 10% arise from the glandular, mucus-secreting cells of the cervical canal leading into the uterus. This cancer is the 2nd most common cancer in women worldwide. The following methods are used for cervical screening/detection:

Pap smear—This screening examination is obtained by collecting a sample of cells from the cervix with a wooden or plastic spatula and brush. Specimens are placed on glass slides and examined by a special pathologist/cytologist. If abnormalities are found, women are typically asked to return for colposcopy. The quality of the Pap smear can be compromised by inflammatory exudate, or failure to sample the transformation zone. As a result, a relatively high false-negative rate of 20% pap smears might cause failure to diagnose pre-invasive disease.

Colposcopy—Colposcopy uses a magnifying lens to view the surface of the cervix under white and green light after a mild vinegar solution is applied. If pathologic areas are seen, a biopsy is taken. This method is not performed in real time and has the disadvantages of other forms of visible light endoscopy as described above. Particular, visible light endoscopy is subjective and depends on physician experience and alertness.

None of the above techniques of detection are capable of positively identifying tumors. Therefore according to current art distinguishing tumors from other benign or pathological conditions requires biopsy. Biopsies have many obvious disadvantages: firstly a biopsy requires intrusive removal of tissue that can be painful and expensive. Particularly in internal cavities and more particularly in the stomach and intestines, biopsies run a high risk of serious complications. These complications can lead to very painful conditions (including ulcers), they can force limiting diet or activity of a patient for significant periods of time and complications may even require treatment and drastic intervention (for instance surgery). Only a very limited number of sites can be biopsied in one session. Furthermore, biopsy samples must be stored and transported to a laboratory for expert analysis. Storage and transportation increase the cost, increase the possibility that samples will be mishandled, destroyed or lost, and also cause a significant time delay in receiving results. This time delay means that examination follow up requires bringing the patient back to the doctor for a separate session. This increases the inconvenience to the patient, the cost and the risk that contact will be lost or the disease will precede to a point of being untreatable. Furthermore, the waiting period causes significant anxiety to the patient. Finally, interpretation of biopsies is usually by microscopic analysis, which results in qualitative subjective results that are not well suited to consistent interpretation.

Therefore, in medical diagnosis, there is great interest improved sensitivity, safe non-operative detection technologies capable of revealing internal cancers in their early stages and also in improved techniques for identification to differentiate between cancer, benign conditions and other pathologies of internal tissue.

Optical methods for have long been applied to early detection and identification of skin cancer [Gniadecka, M., H. C. Wulf, N. Nymark Mortensen, O. Faurskov Nielsen and D. H. Christensen "Diagnosis of Basal Cell Carcinoma by Raman Spectroscopy", JOURNAL OF RAMAN SPECTROSCOPY, 28, 125-129, 1997; Brooks, A., N. I. Afanasyeva, V. Makchine, R. F. Bruch, S. F. Kolyakov, S. Artjushenko and L. N. Butvina, "New Method for Investigations of Normal Human Skin Surfaces in vivo Using Fiber-optic Evanescent Wave Fourier Transform Infrared Spectroscopy (FEW-FTIR) ", Surf. Interface Anal., 27, 221-229, 1999]. Visible light examination, spectral analysis, digital imaging using active regimes, and thermal imaging methods have been applied.

In the spectral regime electromagnetic radiation signal intensities are measured in various frequency bands generally based on perceiving reflected light in the visible to NIR bands. Identification of specific abnormalities is based on information about the corresponding "signature" of radiation associated with the corresponding anomaly measured in the frequency domain.

In skin cancer studies, the method of thermal imaging has been used to produce color images of skin tumors or skin pathological abnormalities. This passive integral regime detects differences in patterns of MIR emissions from normal and pathological tissues. The results of this imaging are generally classified according to certain parameters and used for detection of skin abnormalities and identification of the abnormalities whether they are pathological (e.g. tumors, melanoma, lesions) or benign (nevi). Changes in properties (like temperature of color) mark the boundaries between normal and abnormal (suspected cancerous) regions.

Recently, medium infrared MIR spectral methods have also been used to improve accuracy and reproducibility of biopsy evaluation for both gastric cancer [Naoko Fujioka, Yuji Morimoto, Tsunenori Arai, Makoto Kikuchi, "Discrimination between normal and malignant human gastric tissues by Fourier transform infrared spectroscopy", Cancer Detection and Prevention 28, 32-36, (2004)] and lung cancer [Yang, Y., Josep Sule-Suso, Ganesh D. Sockalingum, Gregory Kegelaer, Michel Manfait, Alicia J El Haj, "Study of Tumor Cell Invasion by Fourier Transform Infrared Microspectroscopy", Biopolymers, Vol. 78, 311-317 (2005); Wang, H. P., H. C. Wangb, and Y. J. Huang, "Microscopic FTIW studies of lung cancer cells in pleural fluid", The Science of the Total Environment 204. 283-287, (1997)]. Samples, for spectral analysis, may be smaller than traditional biopsies. This makes the sampling procedure significantly less traumatic for the patient. Spectral analyzers may even be brought to a doctor's office or an operating room to allow real time diagnosis and treatment considerably increasing the efficiency of treatment as well as reducing expensive and dangerous time delays and reducing the chance of losing contact with patients.

Nevertheless, with the exceptions of visual inspection of reflected visible radiation (endoscopy) (for example see U.S. Pat. No. 6,975,898 B2 Seibel) and some limited research on auto fluorescence spectroscopy (for example see U.S. Pat. No. 5,876,995 Bryan and U.S. Pat. No. 7,172,553 Ueno et al.), optical analytical techniques have not been applied to in-vivo intra-orifice cancer detection and identification. Furthermore current art intra-orifice optical techniques use an active regime, applying radiation in the ultraviolet UV, visible or near-infrared NIR wave bands from an external source and measuring the reflection, absorption, refraction or fluorescence of the rays in the visible spectrum. There may be risks involved in exposing internal tissue to electromagnetic radiation even in the optical spectrum (because internal tissue is not naturally exposed to such radiation). Many of the widely known techniques of detection and identification of external pathologies have disadvantages making them not fully appropriate for detection and identification of internal cancers and cancer precursors. Furthermore new instruments have yet to be developed (and licensed) to permit application of these techniques to internal tissue in-vivo.

Although it has long been known that in-vivo heat differentials can be used to detect and identify cancer both in the lungs [Stefanadis, C., Christina Chrysohoou, Demosthenes B Panagiotakos, Elisabeth Passalidou, Vasiliki Katsi, Vlassios Polychronopoulos and Pavlos K Toutouzas, Temperature differences are associated with malignancy on lung lesions: a clinical study", BMC Cancer, 3:1 doi:10.1186/1471-2407-3-1, (2003)] and in the gastrointestinal tract [Stefanadis C., Christina Chrysohoou, Emmanouel Paraskevas, Demosthenes B. Panagiotakos, Demetrios Xynopoulos, Dimitris Dimitroulopoulos, Kalliopi Petraki, Constantina Papadimitriou, Kyriakos Karoutsos, Christos Pitsavos and Pavlos K. Toutouzas, "Thermal Heterogeneity Constitutes A Marker for the Detection of Malignant Gastric Lesions In Vivo", J Clin Gastroenterol 36(3):215-218, 2003], measurement of heat differentials of internal tissue has been limited to highly complex experimental studies using thermistors which must actually contact the area of measurement. Thermistor based temperature measurement may, in the future, be useful for identification of lesions, but measuring a temperature differential alone is not sufficient for positive identification of specific pathologies. Furthermore, for the purpose of detection, use of a thermistor is not at all feasible. Simply put, it is unthinkable that one would drag a thermistor across the entire inner surface of a subject's intestines to screen for pathologies. On the other hand, the use of heat cameras to sense temperature anomalies, as has been proposed for detecting skin cancer [for example using Forward Looking Infrared Sensors (FLIRS) and MIR pyroelectric cameras] with current art endoscopic techniques is not feasible because these cameras are heat sensitive and too large to be fit into an endoscope. Thus, current art techniques of endoscopic detection, which are based on imaging using a miniature camera located in the endoscope or a doctor using his eyes to detect a visible electromagnetic radiation signal through an optical fiber, are not applicable in the MIR spectrum.

There is thus a widely recognized need for, and it would be highly advantageous to have, a non-invasive methodology to detect and identify pathologic conditions of internal tissue in-vivo. The current invention fills this need.

SUMMARY OF THE INVENTION

The present invention is a method and device for detecting, imaging or identifying pathological lesions inside an orifice of a living subject. More specifically the present invention relates to a method and device for passive detection and identification of different kinds of gastrointestinal tumors, lesions and cancers by combined analyses of visible and infra-red optical signals based on integral and spectral regimes for detection and imaging leading earlier warning and treatment of potentially dangerous conditions.

According to the teachings of the present invention there is provided a method for diagnosing an abnormality in an internal tissue of a living subject. The method includes the steps of placing an instrument inside an orifice of the subject and sensing via the instrument a passively occurring electromagnetic radiation signal inside the orifice. The signal is associated with the abnormality. The diagnosis could include detecting the abnormality, identifying the abnormality or imaging the abnormality. The instrument could include a detector to detect the signal or the instrument could include a pathway by which the signal is transported to an external detector.

According to the teachings of the present invention, there is also provided a method for diagnosing an abnormality in an internal tissue of a living subject. The method includes the steps of placing an instrument inside an orifice of the subject, and sensing via the instrument a medium infrared radiation signal inside the orifice. The signal is associated with the abnormality. Particularly, the signal includes a black body radiation from the abnormality.

According to the teachings of the present invention, there is also provided a device for diagnosing an abnormality in an internal tissue of a living subject. The device includes a sensor configured to sense an electromagnetic radiation signal that is passively occurring inside an orifice of the subject and is associated with the abnormality. The device also includes a delivery system configured to bring together said signal and said sensor.

According to further features in preferred embodiments of the invention described below, it is not know apriori whether there is an abnormality and the method further includes the step of detecting the abnormality according to a result of the sensing.

According to still further features in the described preferred embodiments, the method further includes the step of processing a result of the sensing. Particularly processing can include noise reduction, contrast adjustment or other known signal processing.

According to still further features in the described preferred embodiments, the step of processing includes calculating a differential measure.

According to still further features in the described preferred embodiments, the differential measure quantifies a difference between a background radiation level inside of the orifice and the signal, which is an anomalous radiation level associated with the abnormality.

According to still further features in the described preferred embodiments, the differential measure is a contrast.

According to still further features in the described preferred embodiments, the method further comprising the step of perceiving a visible light reflected from the abnormality.

According to still further features in the described preferred embodiments, the step of perceiving also includes imaging the visible light.

According to still further features in the described preferred embodiments, the step of sensing further includes imaging the passively emitted signal.

According to still further features in the described preferred embodiments, the method also includes the step of measuring a spectrum of the passively emitted signal, and the abnormality is identified as cancerous based on the measured spectrum.

According to still further features in the described preferred embodiments, the sensor is located outside of the orifice and the delivery system transmits the signal to said sensor. For example the signal is transmitted via an optical fiber to an external sensor.

According to still further features in the described preferred embodiments, the delivery system is configured to bring the sensor inside of the orifice.

According to still further features in the described preferred embodiments, the orifice includes an esophagus, a stomach, a bronchia, an intestine, a lung, a colon, a kidney, a cervix, a vagina, an uterus, a fallopian tube, a respiratory tract, a gastrointestinal tract, an urinary tract, a trachea, an artery, a bile duct, a prostate, a testis, a bladder, a rectum, or a nasal cavity.

According to still further features in the described preferred embodiments, the delivery system includes an endoscope, a wireless capsule endoscope, an optical fiber, a lens, a miniature infrared camera, or a prior art endoscope.

According to still further features in the described preferred embodiments, the signal includes a MIR band radiation, a NIR band radiation, a blackbody radiation emitted by the abnormality, a blackbody radiation absorbed by the abnormality, a blackbody radiation reflected by the abnormality, a blackbody radiation emitted by healthy tissue, or a background radiation absorbed by the abnormality.

TERMINOLOGY

For the sake of the present invention, the following definitions are used:

Passively occurring—In a diagnostic procedure, a radiation is said to be passively occurring if the radiation is not produced for the sake of the procedure and is not a result of stimulation by the procedure.

Diagnose—Any one or a combination of the acts of detecting, identifying or imaging of a pathology is defined as diagnosing the pathology.

BRIEF DESCRIPTION OF THE DRAWINGS

The invention is herein described, by way of example only, with reference to the accompanying drawings, where:

FIG. 6b is a close up illustration of the distal tip of the endoscope of the embodiment of FIG. 6a.

DESCRIPTION OF THE PREFERRED EMBODIMENTS

The principles and operation of a non-invasive method and device to identify pathological intra-orifice lesions according to the present invention may be better understood with reference to the drawings and the accompanying description.

Figure 1:
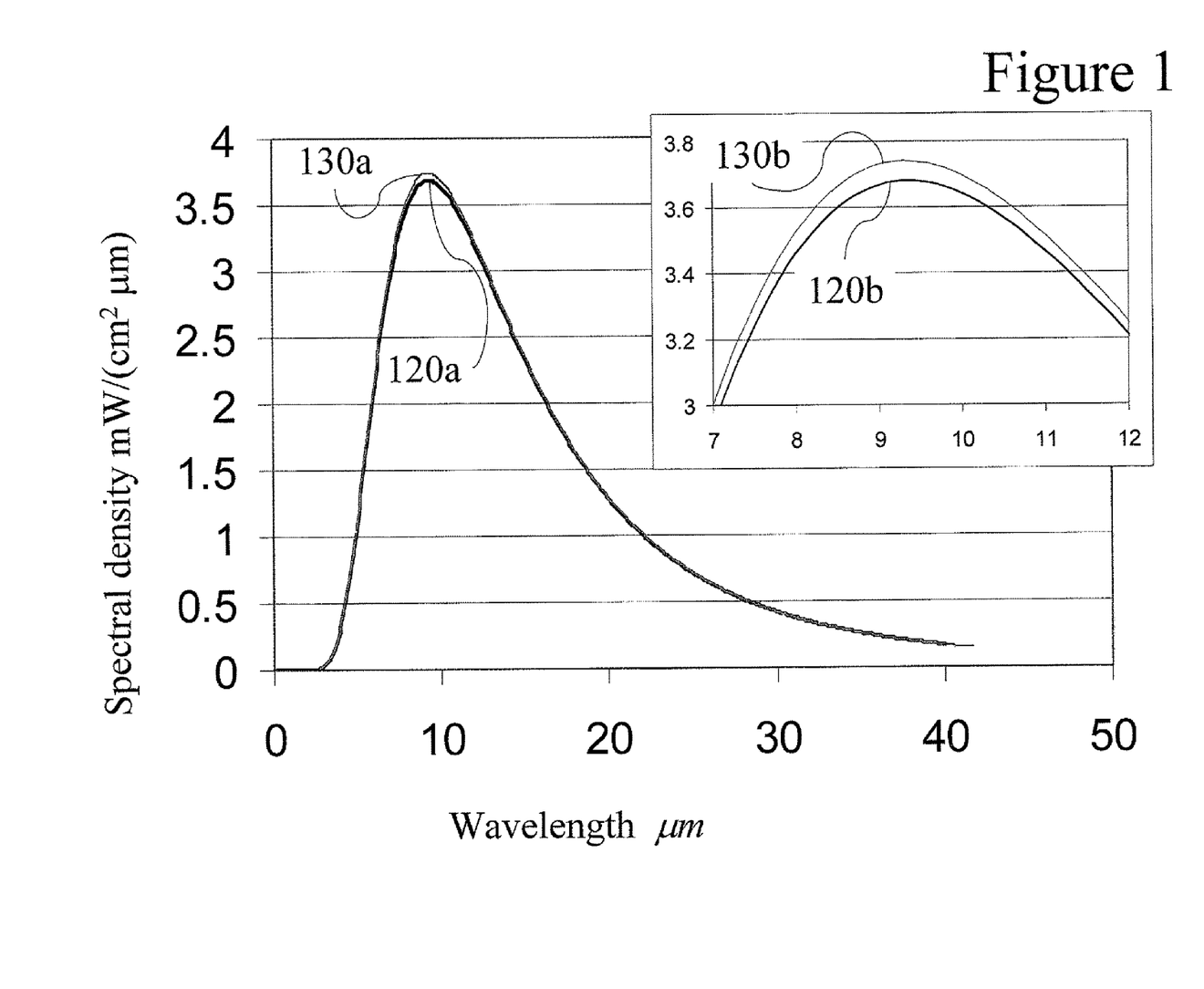
FIG. 1 is a plot of radiation intensity versus wavelength for an ideal black body at temperature 310° and 311° K.

FIG. 1 is a graph showing an electromagnetic radiation signal emitted by an ideal black body, thick lines 120a-b show the spectrum at body temperature (311° K) and thin lines 130a-b show the spectrum at one degrees above body temperature (311° K). The highest power levels are in the MIR band (3-12 μm) although there is measurable radiation in the far infrared FIR region. A one-degree rise temperature difference can easily be detected by the increase in an electromagnetic radiation signal in the 8-12 μm wave band. Such a temperature difference has been found to constitute "a crucial point for the discrimination of malignancy, in bronchial epithelium, with sensitivity (64%) and specificity (91%)" [Stefanadis, C., Christina Chrysohoou, Demosthenes B Panagiotakos, Elisabeth Passalidou, Vasiliki Katsi, Vlassios Polychronopoulos and Pavlos K Toutouzas, Temperature differences are associated with malignancy on lung lesions: a clinical study", BMC Cancer, 3:1 doi:10.1186/1471-2407-3-1, (2003)]. Thus, a MIR Bronchoscope detects and identifies lung cancer in an integral mode by scanning the lungs in the 8-12 μm wave band and detecting increased emittance of a passive MIR electromagnetic radiation signal due to increased temperature of tumors. To increase the detection rate (but at reduced specificity) a smaller temperature difference threshold is used. Similar findings in stomach cancer [Stefanadis C., Christina Chrysohoou, Emmanouel Paraskevas, Demosthenes B. Panagiotakos, Demetrios Xynopoulos, Dimitris Dimitroulopoulos, Kalliopi Petraki, Constantina Papadimitriou, Kyriakos Karoutsos, Christos Pitsavos and Pavlos K. Toutouzas, "Thermal Heterogeneity Constitutes A Marker for the Detection of Malignant Gastric Lesions In Vivo", J Clin Gastroenterol 36(3):215-218, 2003] indicate that a temperature difference of greater than 1.7° K, constitutes a crucial point for the diagnosis of malignancy, in stomach lesions, with sensitivity (72%) and specificity (94%). Thus, in a similar manner an MIR endoscope is used to detect gastric cancer.

Figure 2:
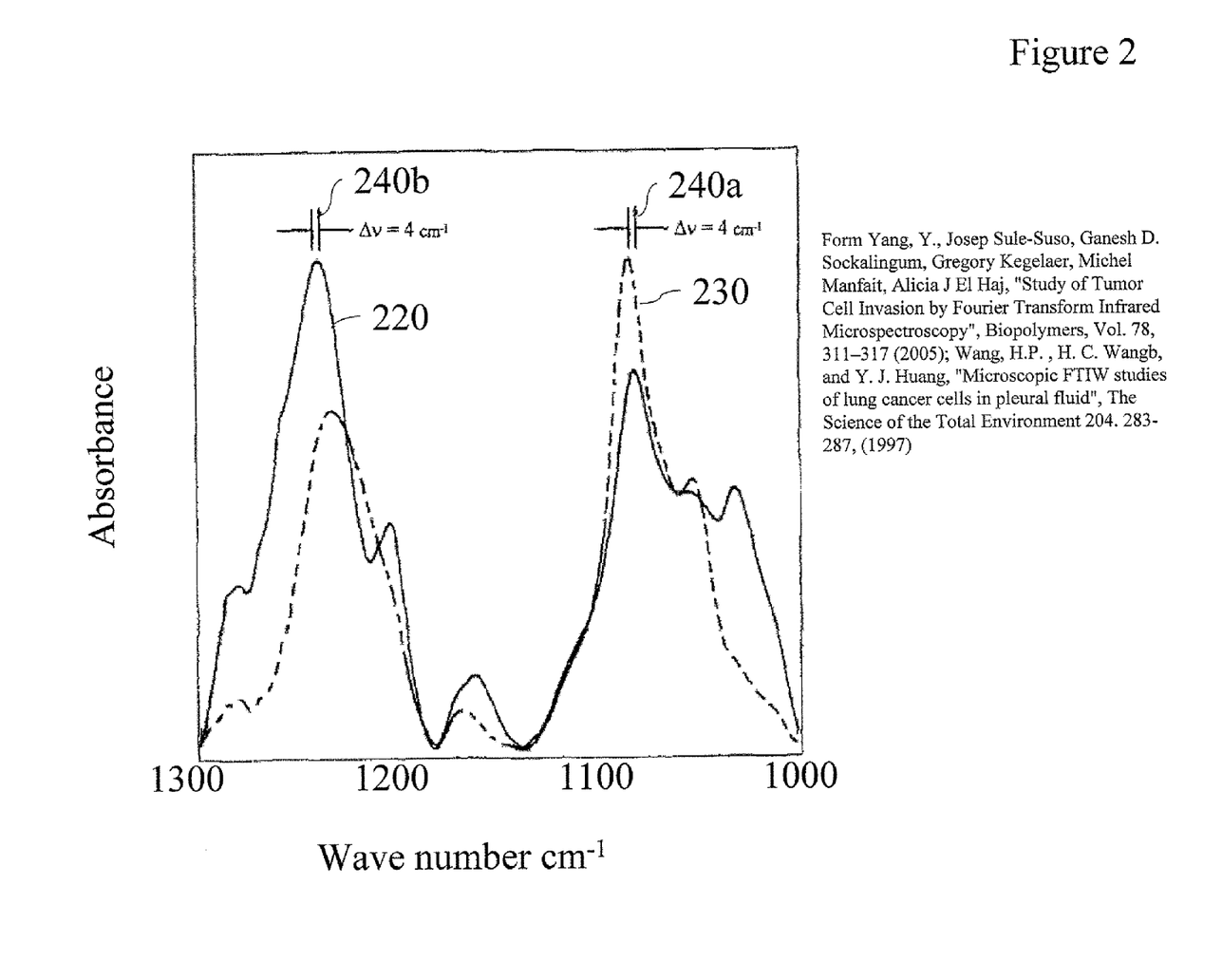
FIG. 2 is a comparison plot of spectral absorbance of healthy and cancerous lung cells.

Increased specificity is achieved by measuring the black body IR emittance spectra of suspected cancerous lesions. Particularly FIG. 2 [Yang, Y., Josep Sule-Suso, Ganesh D. Sockalingum, Gregory Kegelaer, Michel Manfait, Alicia J El Haj, "Study of Tumor Cell Invasion by Fourier Transform Infrared Microspectroscopy", Biopolymers, Vol. 78, 311-317 (2005); Wang, H. P., H. C. Wangb, and Y. J. Huang, "Microscopic FTIW studies of lung cancer cells in pleural fluid", The Science of the Total Environment 204. 283-287, (1997)] shows a healthy lung tissue MIR spectrograph 220 and a cancerous lung tissue MIR spectrograph 230. Cancerous lung tissue spectrograph 220 has an increased absorbance in a 1080 $cm^{-1}$ (9.3 μm) band 240a in comparison with healthy lung tissue spectrograph 220. Furthermore Cancerous lung tissue spectrograph 220 has a decreased absorbance in a 1220 $cm^{-1}$ (8.2 μm) band 240b in comparison with healthy lung tissue spectrograph 220 or tissue from non-cancerous lesions (for example tuberculosis).

The spectral energy density black body electromagnetic radiation signal from on non-ideal black body is given by the formulae $R'(\lambda_i)=\int_{\lambda,ni}^{\lambda+i}[dR(\lambda,T)/d\lambda][\epsilon(\lambda)\tau(\lambda)]d\lambda$ where $dR(\lambda,T)/d\lambda=k_1\lambda^{-5}[\exp(k_2/\lambda T)-1]^{-1}$ and $k_1=3.74\times10^{-16}$ W×m$^4$, k=1.44×10$^{-2}$ m×K; where $dR(\lambda,T)/d\lambda$ is the spectral density of heat flow from the black body at the temperature T (for living human tissue T=310° K); ε is the heat radiation coefficient of blackness of and τ is the transparent coefficient of normal living human tissue. It is important to notice that the intensity of a black body electromagnetic radiation signal is proportional to the blackness of the body. Thus, the intensity of light emitted by a body at a given waveband is proportional to the absorbance in that waveband. Thus FIG. 2, which shows the spectral difference in absorbance between cancerous and healthy lung tissue, also shows the spectral difference in black body radiance between healthy and cancerous lung tissue. Thus, when a high temperature lesion is found in the lung, the lesion is identified as cancerous (or not) by measuring the difference between radiance from the lesion in 1080 $cm^{-1}$ band 240a and 1220 $cm^{-1}$ band 240b. For example defining contrast as $(R_a-R_b)/(R_a+R_b)$ (where $R_a$ is the radiance from the lesion in 1080 cm$^{-1}$ band 240a and R$_b$ is the radiance from the lesion in 1220 cm$^{-1}$ band 240b), then a positive contrast identifies a cancerous lesion while a low contrast identifies a non-cancerous tissue.

Figure 3:
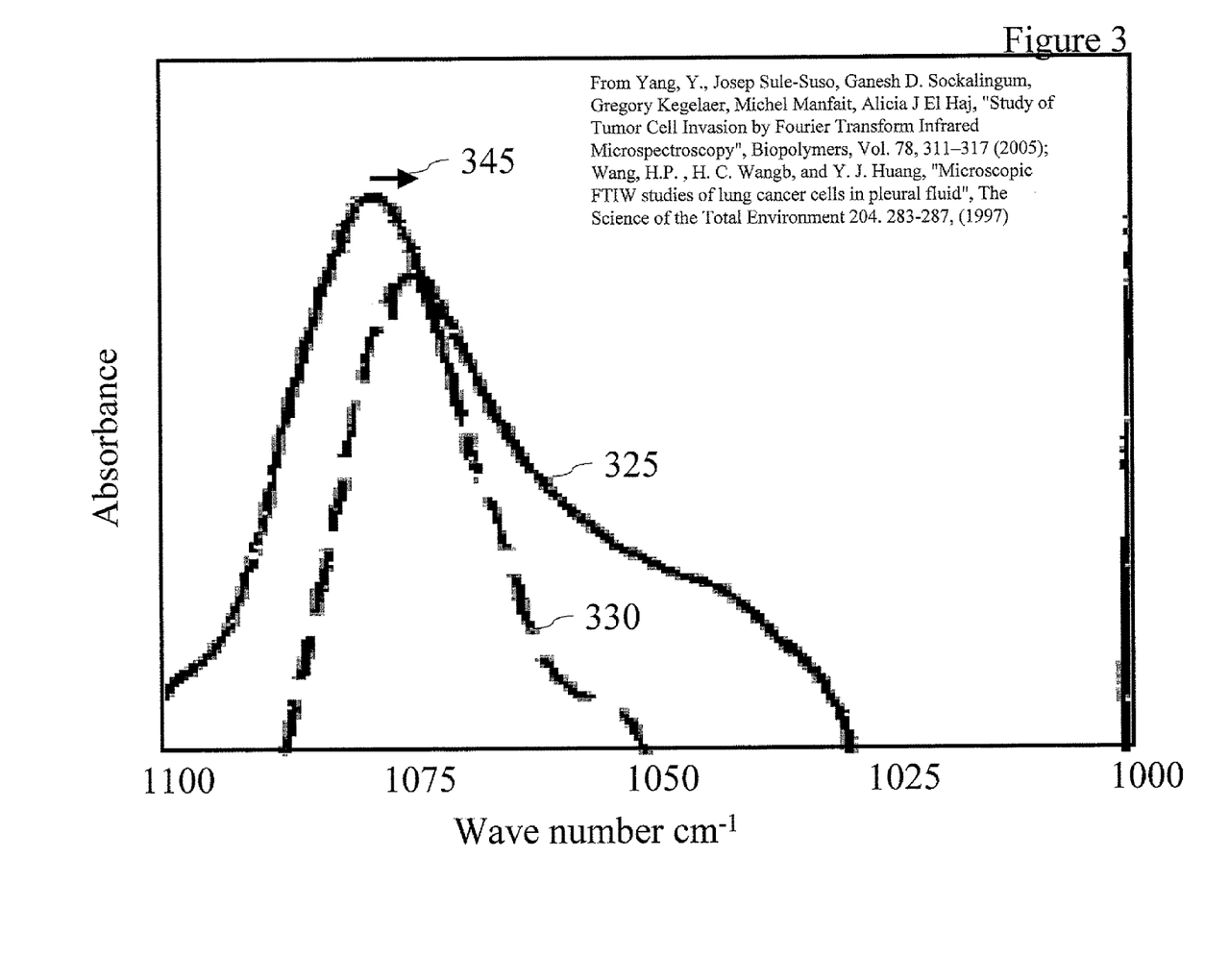
FIG. 3 is a comparison plot of spectral absorbance of tubercular and cancerous lung cells.

Attention is now directed to FIG. 3 [Yang, Y., Josep Sule-Suso, Ganesh D. Sockalingum, Gregory Kegelaer, Michel Manfait, Alicia J El Haj, "Study of Tumor Cell Invasion by Fourier Transform Infrared Microspectroscopy", Biopolymers, Vol. 78, 311-317 (2005); Wang, H. P., H. C. Wangb, and Y. J. Huang, "Microscopic FTIW studies of lung cancer cells in pleural fluid", The Science of the Total Environment 204. 283-287, (1997)], which shows a tubercular lung tissue spectrograph 325. Tubercular lung tissue spectrograph 325 can be differentiated from cancerous lung tissue spectrograph 330 by a blue shift 345 of 6 cm$^{-1}$ in the 1080 cm$^{-1}$ peak. Thus to identify whether an abnormality is cancerous or tubercular, contrast is defined as C=(R$_{1080}$−R$_{1075}$)/(R$_{1080}$+R$_{1075}$) (where R$_{1080}$ is the radiance from the abnormality at 1080 cm$^{-1}$ and R$_{1075}$ is the radiance from the abnormality at 1075 cm$^{-1}$) if the contrast is positive then the abnormality is identified as cancer whereas if the contrast is negative, then the abnormality is identified as tuberculosis.

Figure 4:
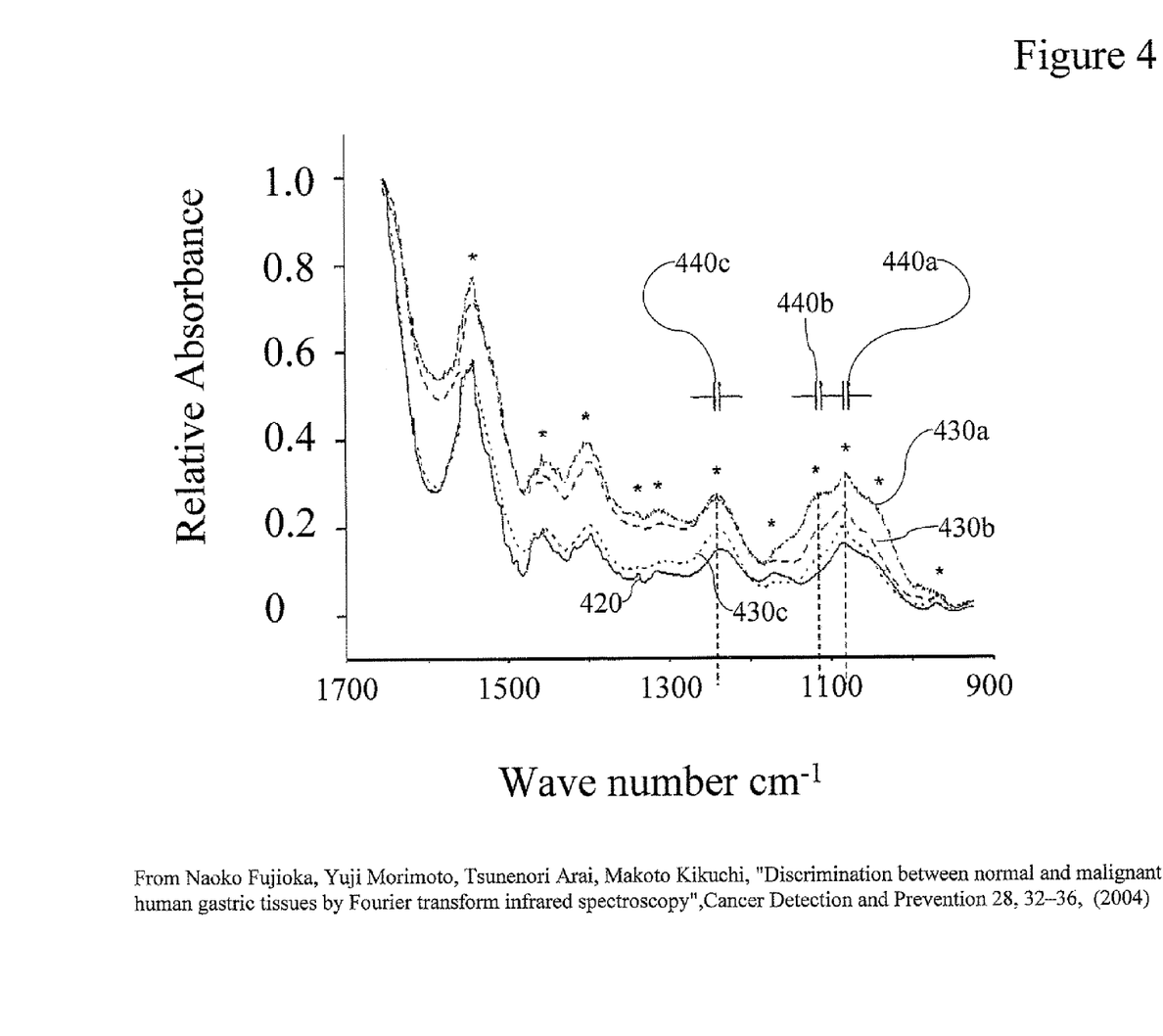
FIG. 4 is a comparison plot of spectral absorbance of healthy and cancerous gastric cells.

Attention is directed to FIG. 4 [Naoko Fujioka, Yuji Morimoto, Tsunenori Arai, Makoto Kikuchi, "Discrimination between normal and malignant human gastric tissues by Fourier transform infrared spectroscopy", Cancer Detection and Prevention 28, 32-36, (2004)], which illustrates a healthy gastric tissue spectrograph 420 (of normal mucosal epithelial cells) and three cancerous gastric tissue spectrographs 430a-c (also of mucosal epithelial cells). Each spectrum was normalized by scaling the entire spectrum to the IR absorbance at 1650 cm$^{-1}$ (amide 1). Asterisks indicate absorption bands. Note the prominent differences in the IR absorbance for band 1240 440c, and band 1120 440b and band 1080 cm$^{-1}$ 440a (dotted lines parallel to y-axis). For all three wavenumber bands 440a-c, all cancer cell spectrographs 430a-c show higher absorbance than normal cells spectrograph 420. Apart from the magnitude of absorbance values, a significant frequency shift occurs between cancer cell spectrographs 430a-c and normal cell spectrograph 420 in 1240 wave band 440c and 1080 cm$^{-1}$ waveband 440a. For 1240 cm$^{-1}$ waveband 440c, peak maximum absorbance in normal cell spectrograph 420 is at 1236.9 cm$^{-1}$ (mean) while cancer cells spectrographs 430a-c show peak: maximum absorbance at 1241.5 cm$^{-1}$ (mean), indicating a 4.6-cm$^{-1}$ shift accompanying malignant alteration. Similarly, peak maximum absorbance in 1080 cm$^{-1}$ waveband 440a shifted from 1081.9 cm$^{-1}$ (normal cell spectrograph 420) to 1085.7 cm$^{-1}$ (cancerous cell spectrographs 430b, c). The increase in absorbance in cancerous cell spectrographs 430a-c compared to normal cell spectrograph 420 in 1080 and 1240 cm$^{-1}$ wavebands 440a,c can be attributed to increased concentration of PO$^{-2}$ phosphodiester (associated by an increased concentration of DNA in cancerous cells). The positive shift in cancerous cell spectrographs 430a-c in 1080 and 1240 cm$^{-1}$ wavebands 440a,c can be attributed to tighter packing of DNA in the nucleus of cancerous cells as opposed to normal gastric cells. The increased peak in 1120 waveband 440b in cancerous cell spectrographs 430a-c compared to normal cell spectrograph 420 can be attributed to higher concentration of RNA in cancerous gastric cells as opposed to normal cells. According to the teachings of the current invention, the above MIR spectra are measured in-vivo allowing identification of cancer cells in-vivo using passive black body radiation naturally emitted by the cells without exposing the patient to potentially dangerous radiation or radioactive tracers of any kind and without requiring the surgical removal of tissue (biopsy).

Figure 5A:
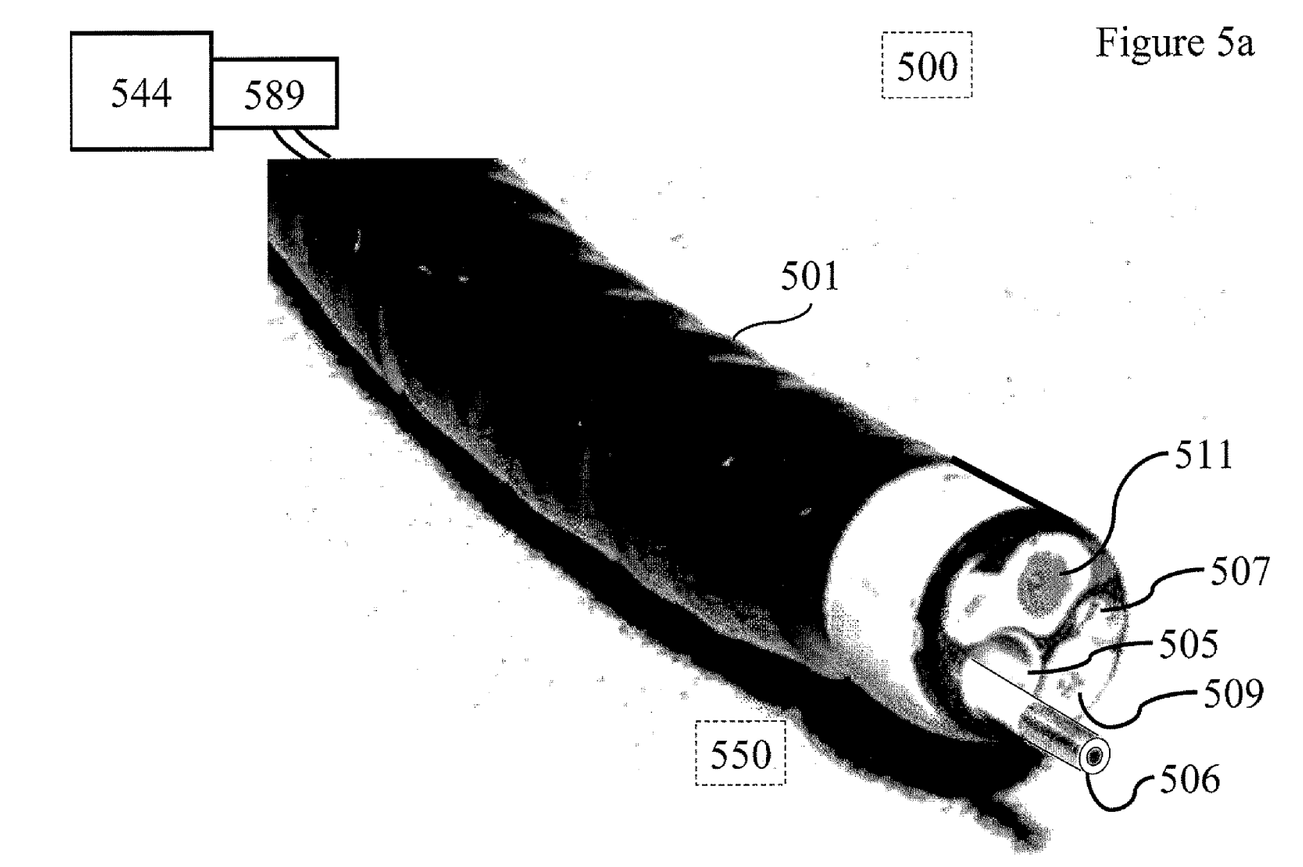
FIG. 5a illustrates a first embodiment of the current invention using an MIR optical fiber inserted into the instrument channel of a current art endoscope.

Attention is now directed to FIG. 5a which illustrates a first embodiment 500 of the current invention in which a MIR optical fiber 506 serves as a delivery system bringing a signal from an orifice of a subject to a MIR sensor 589 [fiber 506 is a silver halide (polycrystalline AgBr$_x$Cl$_{1-x}$) fiber (as is known in the art of FTIR-FEW spectroscopy for example see Brooks, A., N. I. Afanasyeva, V. Makhine, R. F. Bruch, S. F. Kolyakov, S. Artjushenko and L. N. Butvina, "New Method for Investigations of Normal Human Skin Surfaces in vivo Using Fiber-optic Evanescent Wave Fourier Transform Infrared Spectroscopy (FEW-FTIR)", Surf. Interface Anal., 27, 221-229, 1999)]. According to the teachings of the current invention MIR optical fiber 506 is inserted into an instrument channel 505 of a current art endoscope 550. Endoscope 550 also includes a flexible tube 501, a visible light optical fiber serving as a visible illumination channel 507 and a visible light camera 509 for visible light imaging and an air water channel 511. At the proximal end of fiber 506 there is MIR sensor 589 (a standard pyroelectric detector, alternatively sensor could be a bolometric detector or a piroelectric detector or a photon sensitive device, as are well know in the art of MIR detection), which senses MIR signals and passes MIR measurements to a processor 544. Processor 544 also receives output from camera 509 and processor 544 outputs a real time report of the visible image and temperature and MIR contrast to a radiologist operator.

Figure 5B:
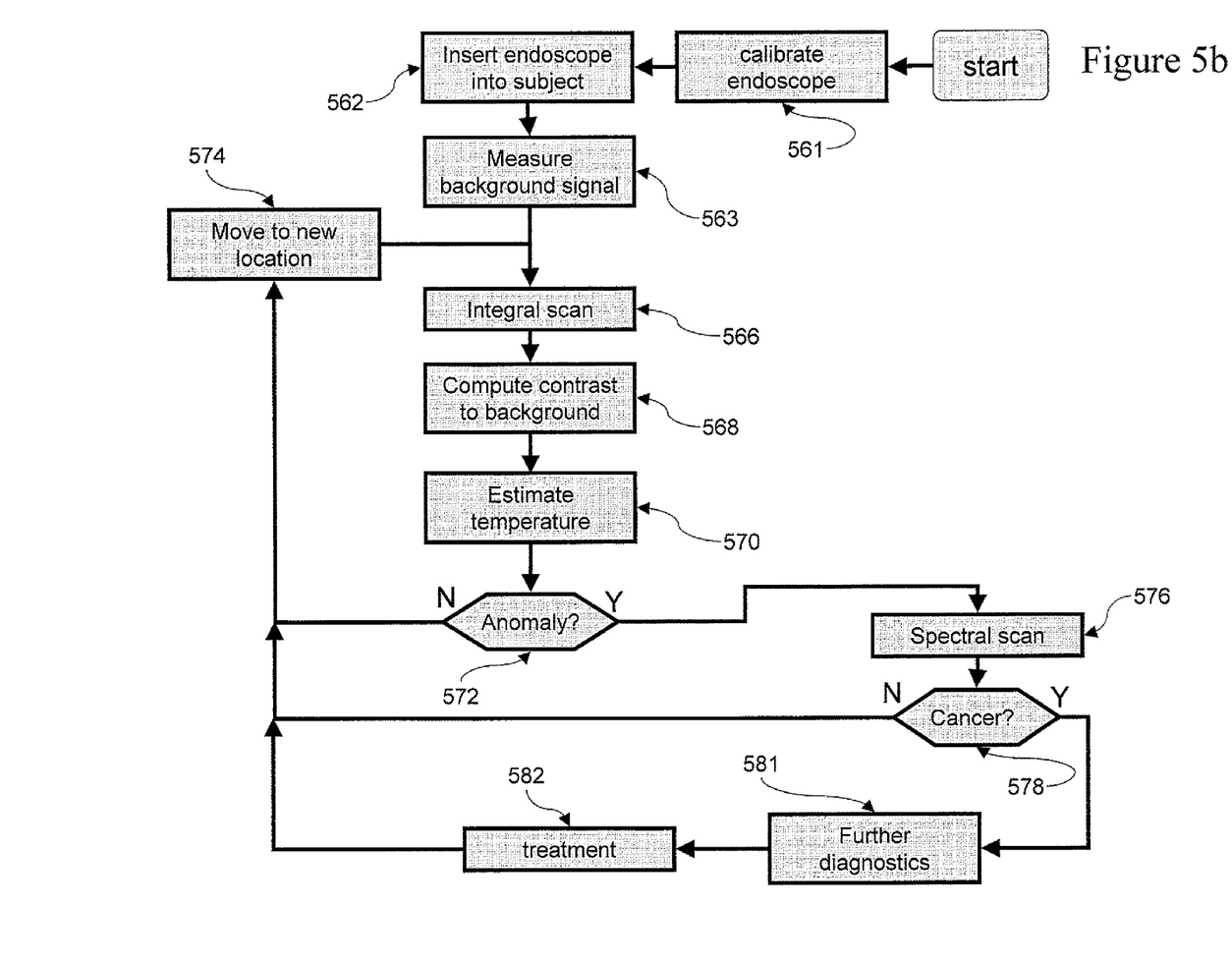
FIG. 5b is a flow chart illustrating a method to detect and identify a cancerous lesion according to the current invention.

Attention is now directed to FIG. 5b, which is a flow chart illustrating a method to diagnose (detect, image and/or identify) a cancerous lesion according to the current invention. The method begins by calibrating 561 the instrument (in the example of FIG. 5b the instrument is endoscope 550) by measuring electromagnetic radiation signals (in a wide band from 7-12 µm) emitted by tissue at different temperatures over 0.5° K intervals from 309-313° K and calculating the response of sensor 589 as a function of the temperature of the tissue. Then endoscope 550 is inserted 562 into a subject. As endoscope 550 passes through the subject [in the example of FIG. 5b endoscope 550 is a sigmoidoscope passing through the intestines of the subject, but in alternative embodiments endoscope 550 could be a proctoscope or a colonoscope or endoscope 550 could be a bronchoscope passing through the lungs or trachea of a subject or a colposcope passing through the vagina and cervix of a subject or a cystoscope passing through the kidney of the subject or a esophagoscope passing through the esophagus of a subject or a gastroscope passing through the stomach and duodenum of a subject or a laparoscope passing through the stomach, liver, other abdominal organs, including female reproductive organs (uterus, ovaries, fallopian tubes) of a subject or a laryngoscope passing through the larynx of a subject or a neuroendoscope passing through the brain of a subject or a thoracoscope passing through the pleura of a subject] and integral background electromagnetic radiation signal levels in a few areas of the intestines having no suspicious abnormalities are quantified 563 in a wide band (spanning from 7-12 µm) (the integral radiation levels at all the location are averaged yielding the average integral background radiation R') and then the spectral background electromagnetic radiation level is measured in narrow bands (for example in the example of FIG. 5b spectral measures are made in three wave-bands $\Delta\lambda_i$ near 1080 cm$^{-1}$=9.25 µm, near 1120 cm$^{-1}$=8.93 µm and near 1240 cm$^{-1}$8.06 µm) at a few locations and the radiation levels in a given wave band are averaged over all locations yielding the average spectral background radiation levels R'$_{9.25}$, R'$_{93}$ and R'$_{8.06}$ respectively). Narrow band quantifications 563 are made by placing an appropriate band-pass filter in front of MIR sensor 589.

After calibrating 561 the instrument and quantifying 563 background radiation levels, then the intestines of the subject are scanned 566 in an integral regime. The integral regime of tissue detection uses information about the gradient of temperature between the normal tissue and the cancerous tissue. For example an integral measure of black body MIR is used to gauge temperature and detect regions of elevated temperature, which are associated with suspected cancerous lesions. Particularly in the example of FIG. 5*b* integral scanning 566 measures the total electromagnetic radiation signal intensity emitted at the location of the distal end of endoscope 550 in the band from 7-12 μm (1430-830 cm$^{-1}$). In alternative embodiments integral scanning 566 includes measuring the spatial distribution of an electromagnetic radiation signal in one or more narrow bands.

Based on previously quantified 562 background radiation level R' processor 544 computes 508 contrast C according to the formula C=(R"−R')/(R"+R') where R" is the measured radiation level at the current location of the distal end of endoscope 550.

Also based on the background radiation level R' (which is assumed to correspond to a normal body temperature of 310° K) and the results of calibration 561*a* processor estimates 570 the temperature of the tissue at the current location of the distal end of endoscope 550.

When the operator determines 572 that by visual inspection that the visual image does not indicate a dangerous abnormality (visual inspection of endoscopic images is well know to those skilled in the art of radiology) and the computed 568 contrast and estimated 570 temperature are not anomalous, then the operator moves 574 endoscope 550 to a new location. On the other hand, if the operator detects an abnormal region by determining that either the visual image or computed 568 contrast or estimated 570 temperature is anomalous, then operator performs 576 a spectral scan.

In the spectral regime, information about the spectral lines or spectral bands of an electromagnetic radiation signal emitted by the tissue are used to seek a "signature" associated with the anomaly in the frequency domain which can be identified as the signature associated a known pathology. The full spectrum from close to far infrared is used for diagnostics the tissue abnormality is used.

Particularly, in the example of FIG. 5*b* in order to identify a cancerous lesion, spectral measurements are performed 576 at the location of the suspicious anomaly in three wave bands $\lambda_i$ (for example in the example of FIG. 5*b* spectral measures are performed 576 in wave-bands near 1080 cm$^{-1}$=9.25 μm, near 1120 cm$^{-1}$=8.93 μm and near 1240 cm$^{-1}$=8.06 μm yielding the spectral radiation levels R"$_{9.25}$, R"$_{8.93}$, and R"$_{8.06}$ respectively).

The normalized heat flow difference (or contrast) is computed in the anomalous zones in the chosen wavelengths with the known narrow waveband $\Delta\lambda_i$ of measurements. The counting of the mean spectral density of the measured heat flows in each band of measuring according the formula $S_{\lambda,i}=R_{\lambda,i}/\Delta\lambda_i$ where $S_{\lambda,i}$ is the mean spectral density of the heat flow for the chosen $\lambda_i$ band (ith wavelength); $R_{\lambda,i}$ is the measured value of the heat flow in the chosen $\lambda_i$ band; $\Delta\lambda_i$ is the spectral width of the chosen ith band.

In spectral regime the contrast in the specific bands are investigated to identify cancerous lesions and differentiate them in the frequency domain, by use of the following formula $C(\Delta\lambda_i)=[R"_c(\Delta\lambda_i)-R'_c(\Delta\mu_i)]/[R"_c(\Delta\lambda_i)+R'_c(\Delta\lambda_i)]$ where R'$_c$ is the background heat flow, R"$_c$ is the heat flow from the region with the anomaly, $\Delta\lambda_i$ is the specific range in the frequency band. The normalized heat flow difference (or contrast) must be measured in the anomalous zones in the chosen wavelengths with the known narrow waveband $\Delta\lambda_i$ of measurements.

Based on the combination of the visual image analysis, integral scan 566, and performance 576 of spectral measurements, the operator identifies 578 a lesion as cancerous or benign. When the lesion is benign, then the operator moves 574 the endoscope to a new location and continues scanning. When the lesion is cancerous the operator executes further diagnostic tests 581 (for example a biopsy) or treatments 582 (for example excision or application of local radiation) removing MIR optical fiber 506 from instrument channel 505 and inserting instruments and by methodologies known in the art of cancer diagnosis and treatment.

Thus the method of the current invention is based on the combination of integral and spectral thermograph analysis of infrared flows radiated by the living tissue surface, the cancerous and the regular tissue. It consists:

1) Measure of the space distribution of the integral flow from the object in a wide spectral band (it is understood that the integral scan could alternatively include one or more narrow band measurements) and estimate the temperature. Existing embodiments of the current invention can detect in the integral mode in-vivo temperature differentials of 0.5° K.

2) Spectral regime based on as spectral density of emitting radiation (dR/d$\lambda$) from human body as a black body. Assuming a background temperature $T_0$=310° K the temperature of a given location is measured using the integral method (above) then in multiple spectral wave bands for identification.

One who is skilled in the art of signal processing will understand that by calculating a differential measure (contrast) rather than just reporting raw measurements, we improve sensitivity to subtle differences in intensity of visible and infrared emission. This improved sensitivity allows precise quantification of changes in light absorption and heat generation that are characteristic of different forms of lesions and stages of cancer development. Therefore the present invention discloses an extremely sensitive method to differentiate between normal cells and those with pathological abnormalities. For example, in embodiments described above, the current invention uses the differential measure (contrast) between the normal cells and cells with pathological abnormalities in an integral regime and a spectral regime of analysis. Spatial distribution of contrast of a wide frequency band is taken into account in the integral regime to detect a lesion and to assess the position, size and shape of the lesion. Frequency dependence of the contrast, its magnitude and its sign are used to assess, vascular and metabolic activity, which are different for normal cells and cells with pathological abnormalities. Combined together, both regimes allow precise diagnostics different abnormalities and facilitate earlier warning of cancerous and precancerous conditions. As a passive method, the proposed invention allows the use non-destructive testing of any abnormality without exposing the subject to foreign radiation.

Figure 6A:
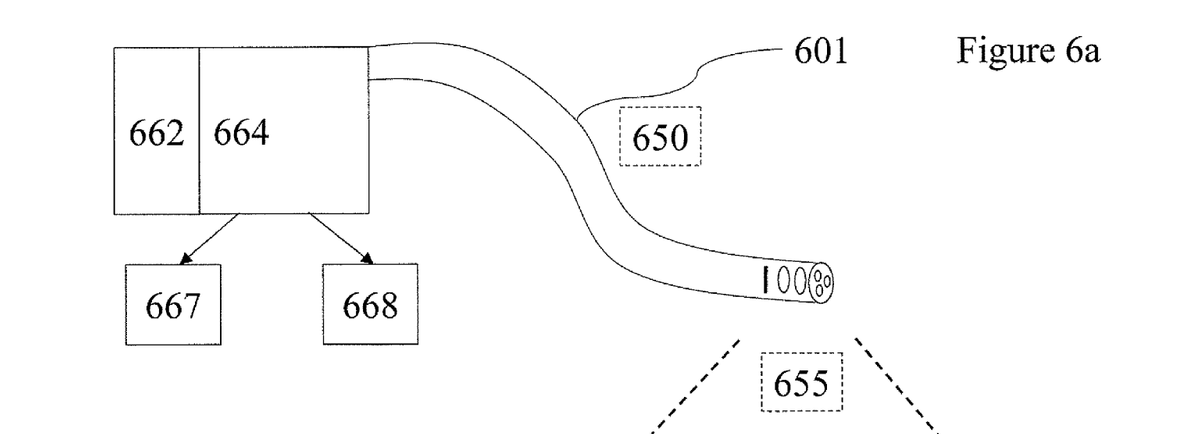
FIG. 6a illustrates a second embodiment of an endoscope according to the current invention having a distal CCD detector.

Attention is now directed to FIG. 6*a*, which illustrates a second embodiment 600 of the current invention. Embodiment 600 includes a custom endoscope 650, a power supply 662 and an image-processing unit 664.

Figure 6B:
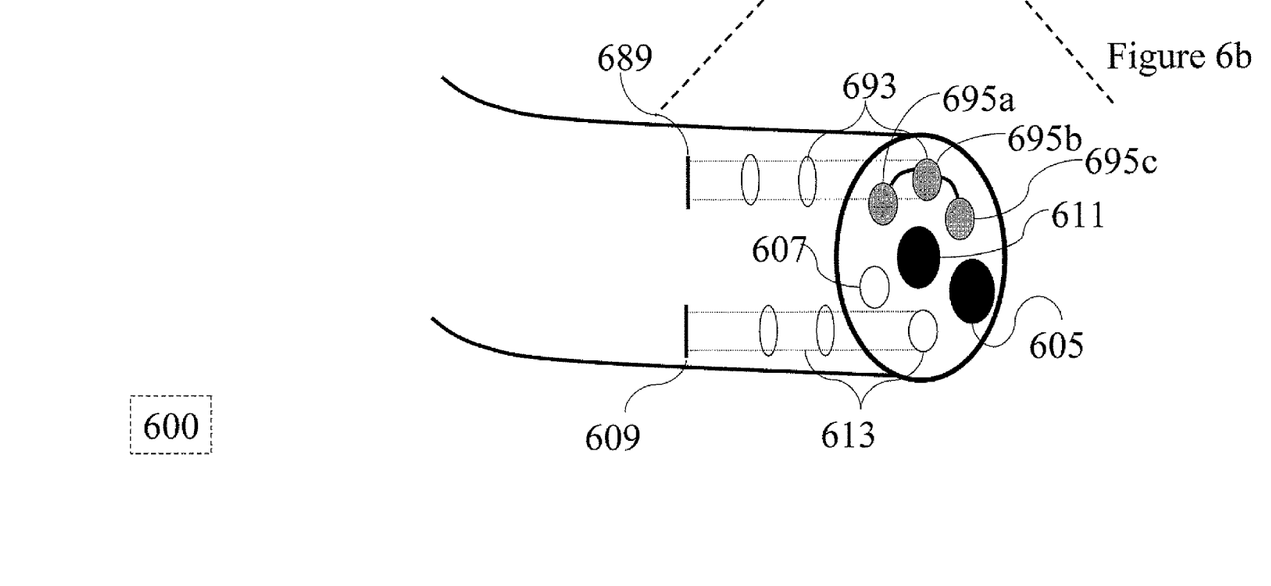

Endoscope 650 includes a flexible tube 601, which serves as a delivery system to bring a distal end 655 into an orifice. An enlarged schematic drawing of distal end 655 is shown in FIG. 6*b*. A mid-infrared camera, sensor 689 based on micro bolometric or pyroelectric detector array captures an infrared image 667 and a conventional visible camera 609 captures visible light image 668. Three rotating infrared filters 695*a*-*c* are used to enable MIR spectral measurements. In addition to capturing image frames in the visible and mid-infrared spectral regions, endoscope 650 includes a visible light source 607, an air-water channel 611 and a small instrument channel 605 for taking samples of suspicious tissues through the endoscope. Flexible tube 601 is inserted through the mouth or anus by the same method as it is done by current art visible endoscopes at present.

The flexible guide consist of five channels:
1) Mid-IR channel 693, which includes a window in the distal tip and a series of optical elements in a wide field configuration, all are transparent in the mid-IR spectral range (like Zinc Selenide, Silver halide and others), microbolometric CCD sensor 689 and three rotating filters 695*a-c*.
2) Visible channel 613, which is similar to mid-IR channel 693 except that the materials of the components are transparent in the visible spectral range and visual color imaging is used rather than MIR imaging and spectral measurements.
3) Air/Water channel 611, which delivers air, water or to suction intraluminal contents.
4) Illumination channel/visible light source 607, which provides illumination in the visible spectral range to the suspected tissue.
5) Instrument channel 605, which provides the physician tools to take samples from suspected tissues.

Power supply 662 maintains the mid-IR detector, the visible detector and the illumination unit in operational mode.

Image processing unit 664 processes and delivers the images (667 and 668), which are captured by sensors (609 and 689). In the example of embodiment 600, image-processing unit 664 is a standard personal computer containing image-processing algorithms well known in the current art. In the example of embodiment 600 image-processing unit 664 performs a contrast algorithm to improve the probability of detection.

One who is skilled in the art of endoscopic imaging will understand that locating sensor 669 in distal end 665 of endoscope 650 allows capture of high quality MIR video images (not just local measurements of MIR radiation intensity as in measured by embodiment 500). Thus when using endoscope 650 to detect and identify an internal pathology MIR and visible images are used to discern various parameters of the pathology in the MIR and visual spectrum (for example asymmetry of the shape of the lesion, bordering of the lesion, color of the lesion and dimensions of the lesion). This allows earlier detection of cancerous and precancerous lesions, more precise identification of lesions and staging pathologies than visible imaging or local MIR measurements alone.

Figure 7:
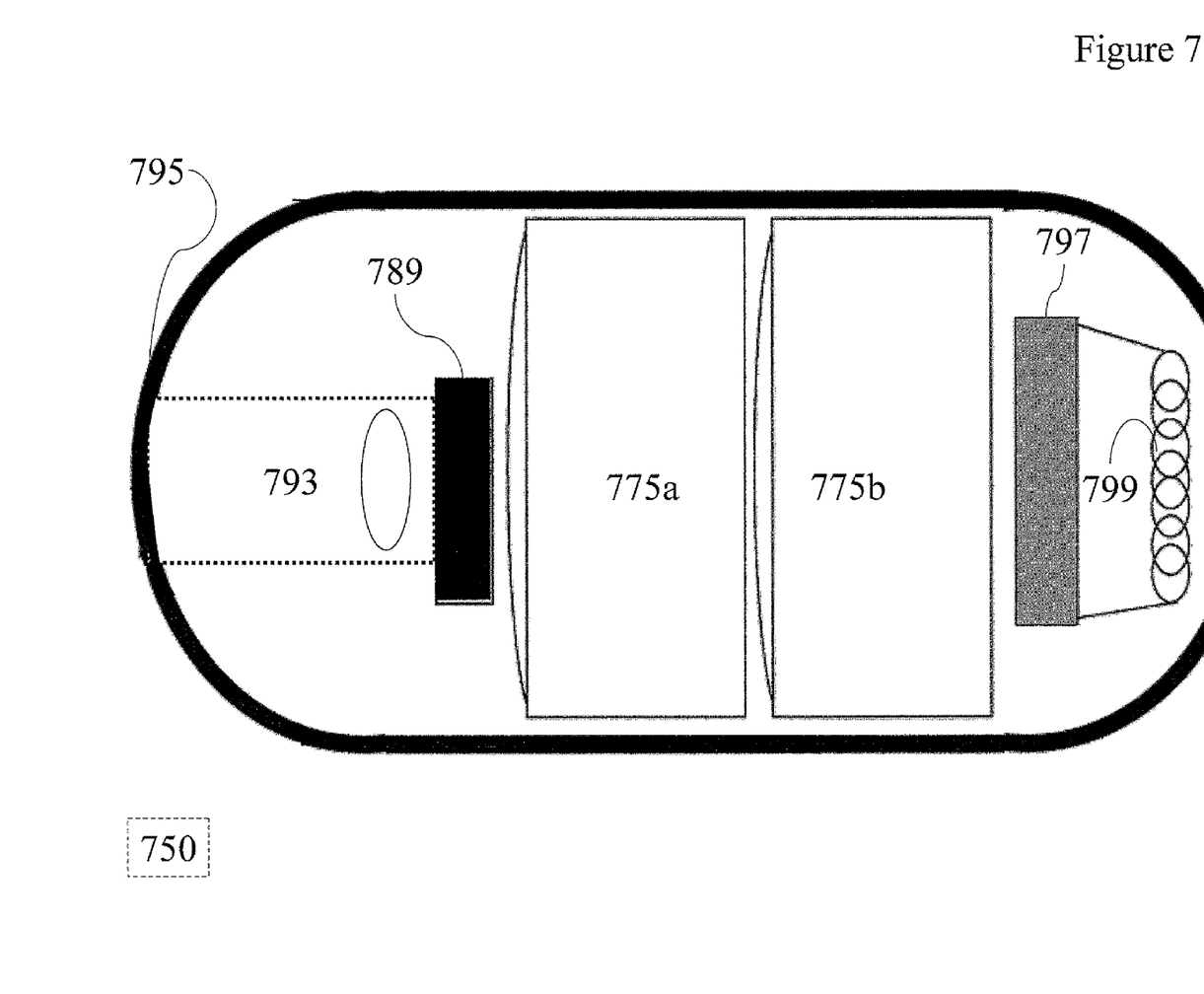
FIG. 7 illustrates a third embodiment of the current invention including a wireless capsule endoscope.

Attention is now directed to FIG. 7, which illustrates a third embodiment of the current invention. The embodiment of FIG. 7 is a wireless capsule endoscope 750 having a batteries 775*a-b* which power a mid-infrared sensor 789 producing MIR images through a mid-MIR channel 793 and mid-MIR transparent dome 795. Endo scope 750 also includes a transmitter 797 and antennae 799 to transmit images to a signal-processing unit outside the subject. It is understood that unlike previous art capsule endoscopes, wireless capsule endoscope 750 detects passively irradiated blackbody MIR, therefore wireless capsule endoscope 750 does not requires a light source and thus, endoscope 750 requires less power than previous art capsule endoscopes. Therefore, batteries 775*a-b* are smaller those of previous art capsule endoscopes. One skilled in the art of wireless capsule endoscopes will realize that it is possible to add a receiver and actuator to endoscope 750 and use endoscope 750 for various active regimes of measurement or treatment (for example self mobility, storing chemicals and applying treatments, and spectral measurements via multiple filters). It is also possible to add a visible light source and detector for more reliable detection and identification of pathologies.

It will be appreciated that the above descriptions are intended only to serve as examples and that many other embodiments are possible within the spirit and the scope of the present invention.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for revealing an abnormality in live internal tissue of a living subject while exposing the subject to no potentially dangerous radiation or radioactive tracers of any kind, requiring no surgical removal of tissue, the method comprising the steps of:
   a) placing an instrument inside an orifice of the living subject, said instrument configured to provide at least an integral regime scan and spectral regime scan of target tissue;
   b) detecting the abnormality by sensing, via said instrument, a passively occurring electromagnetic radiation signal naturally emitted by the cells inside said orifice, said signal being associated with the abnormality;
   c) computing gradient temperature contrast of said target tissue to a normal tissue;
   d) estimating a temperature of said target tissue based on said temperature contrast;
   e) determining if said target tissue is abnormal based on a visual inspection of a visual image of said target tissue, said temperature contrast and said estimated temperature;
   f) if anomaly, measuring a spectrum of said naturally emitted passively occurring electromagnetic radiation signal, and
   d) identifying the abnormality based on a result of said measuring;

wherein said measuring a spectrum includes investigating a contrast (C) in specific bands so as to identify a cancerous lesion and differentiate said cancerous lesion in the frequency domain, by use of the following formula:

$$C(\Delta\lambda i)=[R''c(\Delta\lambda i)-R'c(\Delta\lambda i)/R''c(\Delta\lambda i)+R'c(\Delta\lambda i)]$$

where R'c is a background heat flow, R''c is a heat flow from said target tissue and $\Delta\lambda i$ is a specific range in the frequency band.

2. The method of claim 1, wherein said temperature contrast is computed using the formula $C=(R''-R')/(R''+R')$ where R'' is the measured radiation level of said target tissue and R' is an integral background radiation level.

3. The method of claim 1, further comprising the steps of
   e) providing a source of visible light, and
   f) perceiving a reflection of said visible light from the abnormality, and
wherein the abnormality is identified based on a result of said perceiving.

4. The method of claim 3, wherein said step of perceiving further includes imaging said visible light.

5. The method of claim 1, wherein said step of sensing further includes imaging said passively occurring electromagnetic radiation signal.

6. The method of claim 1, wherein said sensing is of a narrow band of said passively occurring electromagnetic radiation signal.

7. The method of claim 6, wherein said narrow band consists of at least one waveband substantially equal to a wavelength selected from the group consisting of 9.3 micrometers, 8.2 micrometers, 8.05 micrometers and 8.9 micrometers.

8. The method of claim 1, wherein said identifying includes processing a result of said sensing and wherein said processing includes calculating a contrast between a radiance in a first wave band and a radiance in a second wave band.

* * * * *